US007744558B2

(12) United States Patent
Maag

(10) Patent No.: US 7,744,558 B2
(45) Date of Patent: Jun. 29, 2010

(54) PILL PLUNGER

(76) Inventor: R. John Maag, 513 S. Farmer St., Otsego, MI (US) 49078

( * ) Notice: Subject to any disclaimer, the term of this patent is extended or adjusted under 35 U.S.C. 154(b) by 52 days.

(21) Appl. No.: 12/157,126

(22) Filed: Jun. 6, 2008

(65) Prior Publication Data

US 2008/0302816 A1 Dec. 11, 2008

Related U.S. Application Data

(60) Provisional application No. 60/933,311, filed on Jun. 6, 2007.

(51) Int. Cl.
*A61M 31/00* (2006.01)

(52) U.S. Cl. .......... 604/57

(58) Field of Classification Search .......... 604/19
See application file for complete search history.

(56) References Cited

U.S. PATENT DOCUMENTS 3,780,735 A 12/1973 Crouter et al.
4,060,083 A 11/1977 Hanson
5,906,599 A 5/1999 Kaldany
6,162,203 A * 12/2000 Haaga .......... 604/272
6,712,784 B2 3/2004 Huang
6,786,883 B2 9/2004 Shippert
7,491,187 B2 * 2/2009 Van Den Berghe et al. ... 604/66

* cited by examiner

*Primary Examiner*—Nicholas D Lucchesi
*Assistant Examiner*—Pritesh Patel
(74) *Attorney, Agent, or Firm*—Wallace Intellectual Property PLC; Donald J. Wallace

(57) ABSTRACT

A pill plunger includes a hollow tube having a forward end and a rearward end. A rod or plunger has a forward end having a dished out portion for receiving medication and a rearward end having a button. The plunger occupies the tube with the dished out portion at the forward end of the tube and the button extending from the rearward end of the tube. Medication is placed in the dished out portion, which is then retracted into the tube. After insertion of the tube into a patient's mouth, the button is depressed to extend the plunger and dispense the medication. A spring can be used to retract the plunger upon release of the button. The dished out portion can be sealed to carry a fluid or powder. A dual dished out portion can be provided in the rod, and a window can be formed in the hollow tube.

12 Claims, 6 Drawing Sheets

PILL PLUNGER

CROSS-REFERENCE TO RELATED APPLICATIONS

This application claims the benefit of U.S. Provisional Application Ser. No. 60/933,311, filed Jun. 6, 2007, which is incorporated herein in its entirety.

FIELD OF THE INVENTION

The invention is related to devices for administering medications by mouth. More specifically, the invention is related to administering oral medications to difficult or uncooperative patients or patients requiring enhancement or encouragement of the swallowing reflex.

BACKGROUND OF THE INVENTION

Medication administering devices, which allow medical or veterinary personnel to administer medications to uncooperative patients, are known. In the prior art devices, the medication is commonly held within a tubular applicator having an opening either restricted in size or containing a resilient member for holding the solid medication within the tube. Medication, normally in the form of a solid pill, is then ejected from the tube by a plunger activated in the manner of a syringe. These prior art devices do not provide the capability to apply either powdered or liquid medications, and are very specific in the size and/or shape of solid pill that they can accommodate.

It would be advantageous to provide a device for administering medication that can accommodate a wide range of pill sizes in addition to powder or liquid medications.

SUMMARY OF THE INVENTION

A pill plunger includes a hollow tube having a forward end and a rearward end. A rod or plunger has a forward end having a dished out portion for receiving medication and a rearward end having a button. The plunger occupies the tube with the dished out portion at the forward end of the tube and the button extending from the rearward end of the tube. Medication is placed in the dished out portion, which is then retracted into the tube. After insertion of the tube into a patient's mouth, the button is depressed to extend the plunger and dispense the medication. A spring can be used to retract the plunger upon release of the button. The dished out portion can be sealed to carry a fluid or powder. A dual dished out portion can be provided in the rod, and a window can be formed in the hollow tube.

DETAILED DESCRIPTION OF THE INVENTION

Figure 1:
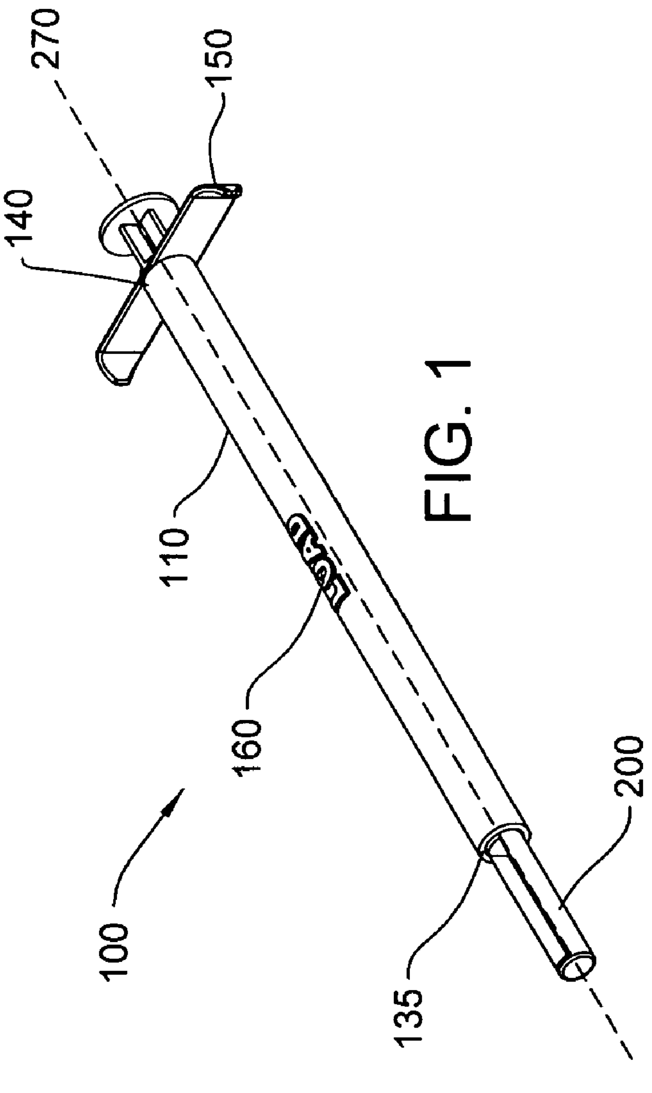
FIG. 1 is a perspective view of a pill plunger according to the invention.
Figure 2:
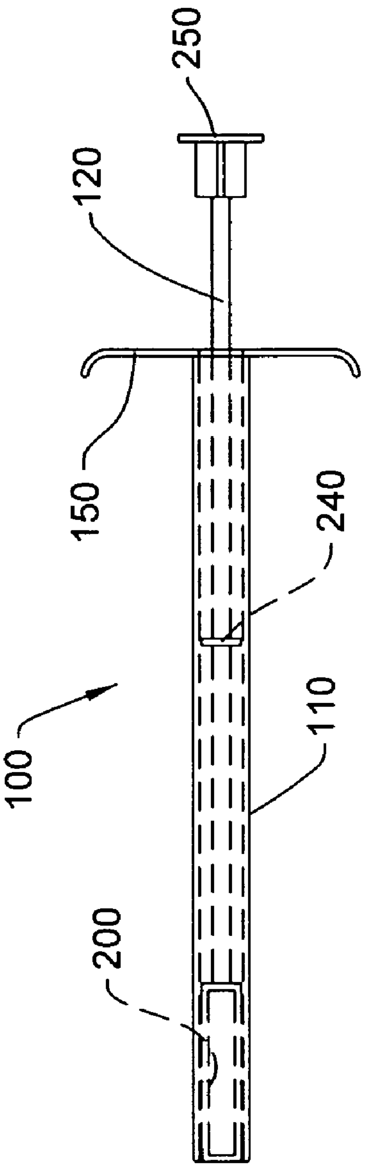
FIG. 2 is a cross-sectional plan view of the pill plunger of FIG. 1.

Referring to FIGS. 1-2, a pill plunger 100 according to the invention comprises a housing 110 in the form of a hollow tube. A plunger insert 120 is received within the housing 110.

Figure 3:
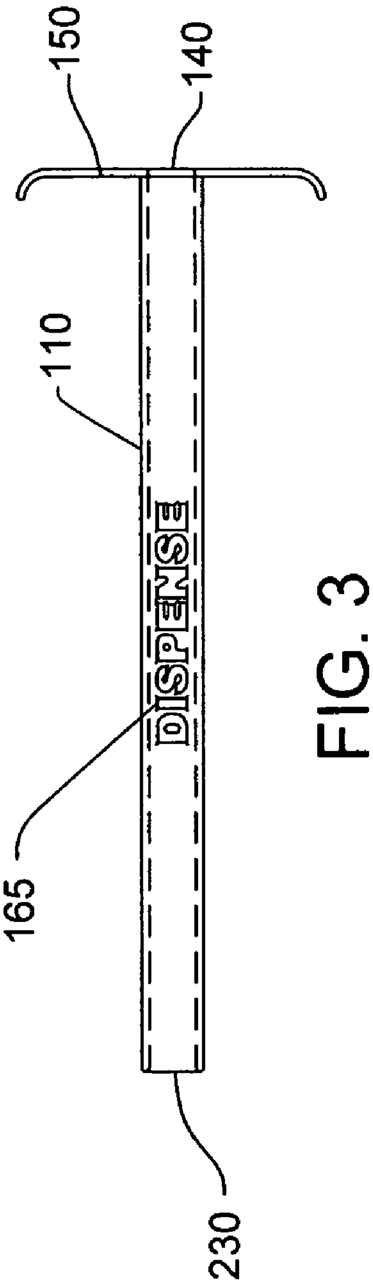
FIG. 3 is a plan view of a reverse side of the housing of the pill plunger of FIGS. 1-2.

The housing 110 includes a hollow tube portion 130. The hollow tube portion 130 has a distal end 135 and a proximal end 140. A pair of finger rests or flanges 150 extend normally from the proximal end 140 of the hollow tube portion 130. Indicia 160, 165 are provided on an external surface of the hollow tube portion 130. The indicia, shown in the drawings as "LOAD" and "DISPENSE" (FIG. 3) are provided on opposing sides of the housing 110.

Figure 4:
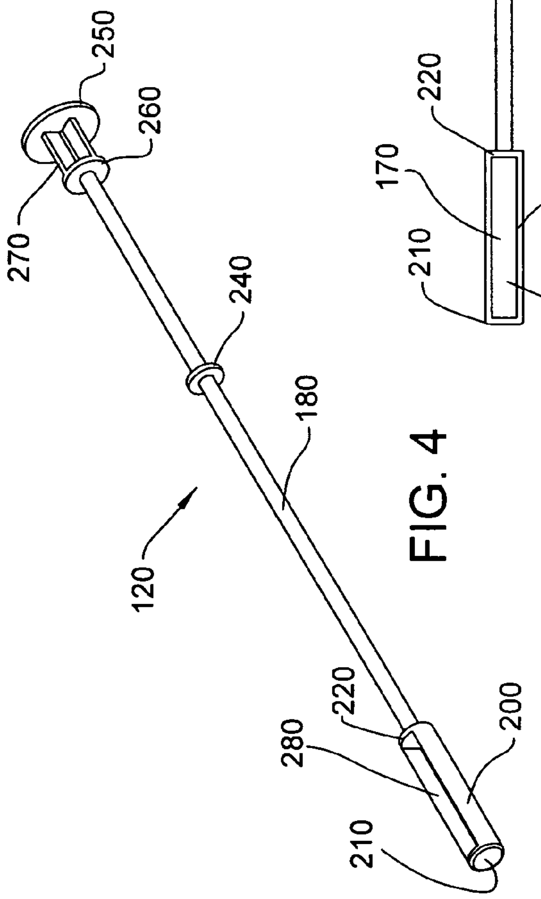
FIG. 4 is a perspective view of a plunger insert for the pill plunger of FIGS. 1-3.
Figure 5:
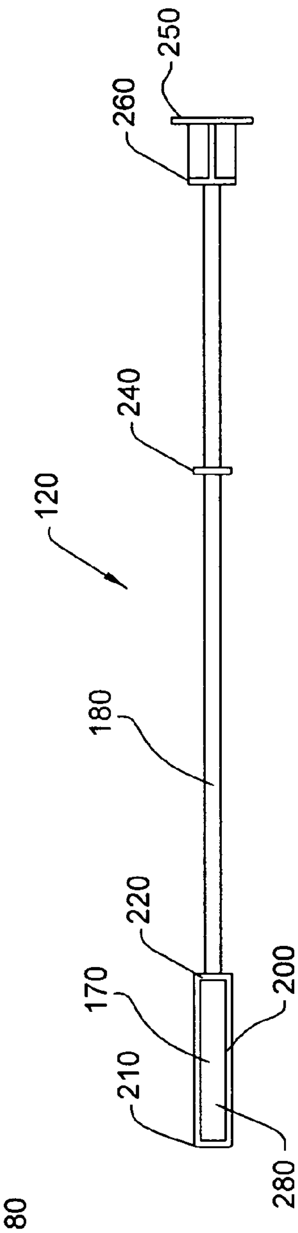
FIG. 5 is a plan view of the plunger insert of FIG. 4.
Figure 6:
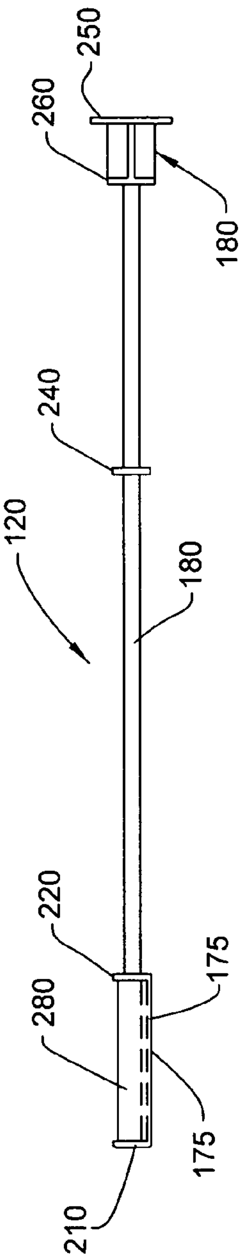
FIG. 6 is a side view of the plunger insert of FIGS. 4-5.
Figure 7:
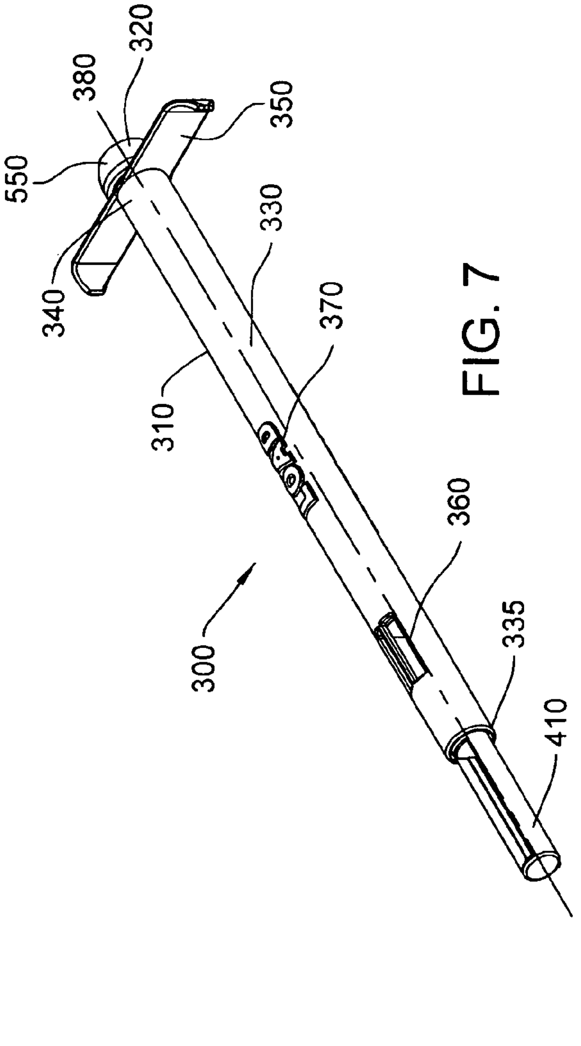
FIG. 7 is a perspective view of a further embodiment of the pill plunger according to the invention.
Figure 8:
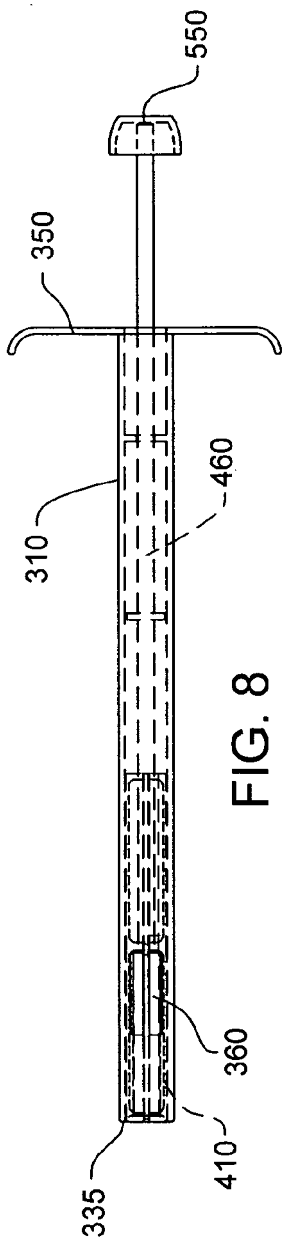
FIG. 8 is a plan view of the pill plunger of FIG. 7.

Referring to FIGS. 4-6, the plunger insert 120 includes a receptacle portion 170, a rod portion 180 and a thumb button portion 190. The receptacle portion 170 is positioned at a distal end 175 of the plunger insert 120. The receptacle portion includes a semi-cylindrical perimeter wall 200, a distal end wall 210 and a proximal end wall 220. The rod portion 180 is attached to or formed integrally with the proximal wall 220 of the receptacle portion 170. Each of the distal wall 210 and the proximal wall 220 of the receptacle portion 170 are generally circular in shape and are sized to closely conform to an inner wall surface 230 of the hollow tube portion 130 of the housing 110. The rod portion 180 is attached to the proximal wall 220 of the receptacle portion 170 in a centered position, and includes a disk-shaped stabilizer 240 for centering the rod portion 180 within the interior of the housing 110. The thumb button portion 190 includes a thumb rest 250 and a plunger stop 260. The thumb rest 250 and plunger stop 260 are joined by integrally formed braces 270. The thumb rest 250 is sized to comfortably receive an operator's thumb, while the plunger stop 260 is sized to be larger than the opening of the hollow tube portion 130, thereby preventing entry of the thumb portion 190 into the hollow tube portion 130. The rod portion 180 is connected to or integrally formed with the plunger stop 260, and is centered thereon for alignment with the housing 110.

The pill plunger 100 is assembled by insertion of the plunger insert 120 into the housing 110. The plunger insert is rotated about a central axis 270 so that an opening 280 of the receptacle portion 170 is facing upward, and the "LOAD" indicia on the hollow tube portion 130 is visible. The plunger insert 120 is then inserted into the housing 110 from the proximal end 140 until the plunger stop 260 abuts the proximal end 140 of the housing 110 and the receptacle portion 170 extends from the distal end 135 of the housing 110. The pill plunger 100 is then ready for accepting a pill or other medication in the receptacle portion 170.

The pill or medication can be in the form of a solid, a powder, or a liquid. In the case of a liquid, the distal wall 210 and the proximal wall 220 of the receptacle portion 170 must be closely fitted to the inner wall surface 230 of the hollow tube portion 130, in order to form a seal sufficient to prevent leakage of the liquid. In the alternative, a groove can be formed in the edge of each wall 210, 220, and a seal, such as an o-ring, placed therein.

After placement of the medication in the receptacle portion 170, the plunger insert 120 is withdrawn toward the proximal end 140 of the housing 110 so that the receptacle portion 170 retracts within the distal end 135 of the housing 110. The pill plunger 100 can then be rotated about the central axis 270 until it is inverted, i.e. the "DISPENSE" indicia is exposed. The pill plunger 100 can then be inserted into a patient's mouth until the distal end 135 of the housing 110 is in a position to dispense the medication. The operator of the pill plunger 100 will necessarily be holding the pill plunger, such that the pill plunger 100 is being held by the finger rests or flanges 150, for example by the user's index and middle fingers, and the user's thumb is resting on the thumb rest 250 of the thumb button portion 190, in the manner of a syringe. Once the pill plunger 100 is in place, the user can then depress the thumb button portion 190 until the plunger stop 260 abuts the proximal end 140 of the pill plunger 100. The receptacle portion 170 is thus fully extended from the distal end 135 of the housing 110 and the medication is thus released from the now inverted receptacle portion 170, having its opening 280 facing downwardly.

In a further embodiment of the invention, shown in FIGS. 5-8, a pill plunger 300 includes a housing 310 and a plunger insert 320. The plunger insert 320 is received within the housing 310.

Housing 310 is formed of a hollow tube 330 having a distal end 335 and a proximal end 340. Outwardly extending flanges or finger rests 350 are mounted to or integral with the hollow tube 330 at its proximal end 340. A window opening 360 is provided in the side of the hollow tube 330 near its distal end 335. The window 360 is provided on a face of the hollow tube 330 corresponding to "LOAD" indicia 370 formed or provided on the surface of the hollow tube 330. "DISPENSE" indicia 375 is provided on an opposing outer surface of the hollow tube 330, 180 degrees remote from the "LOAD" indicia, about an axis 380 running longitudinally through the pill plunger 300.

The plunger insert 320 has a distal end 390 and a proximal end 400. A dual receptacle portion 420 is positioned at the distal end 390 of the plunger insert 320. The receptacle portion 410 has a semi-cylindrical side wall 420, a distal end wall 430, an intermediate wall 440 and a proximal end wall 450. A rod portion 460 of the plunger insert 320 is connected to or integral with the receptacle portion 410 and is attached at the center of the circular proximal end wall 450. The rod portion 460 further includes a disk-shaped stabilizer 470.

Figure 9:
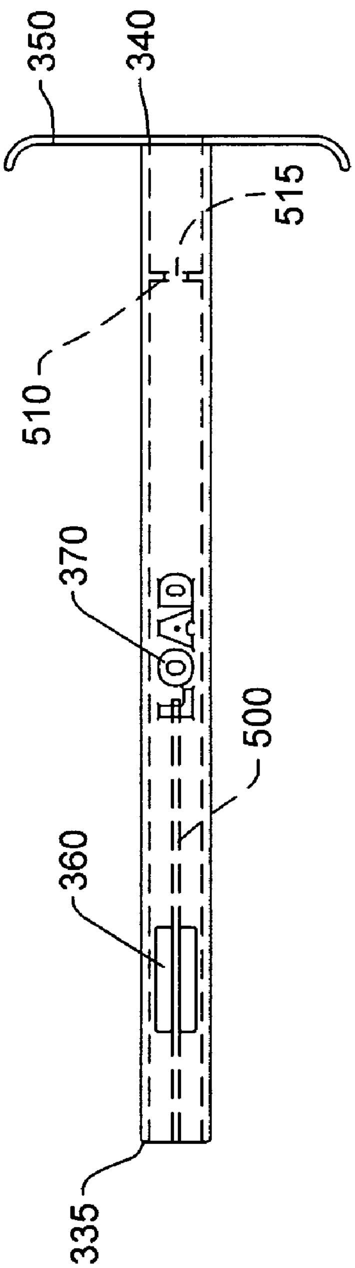
FIG. 9 is a plan view of the housing for the pill plunger of FIGS. 7-8.
Figure 10:
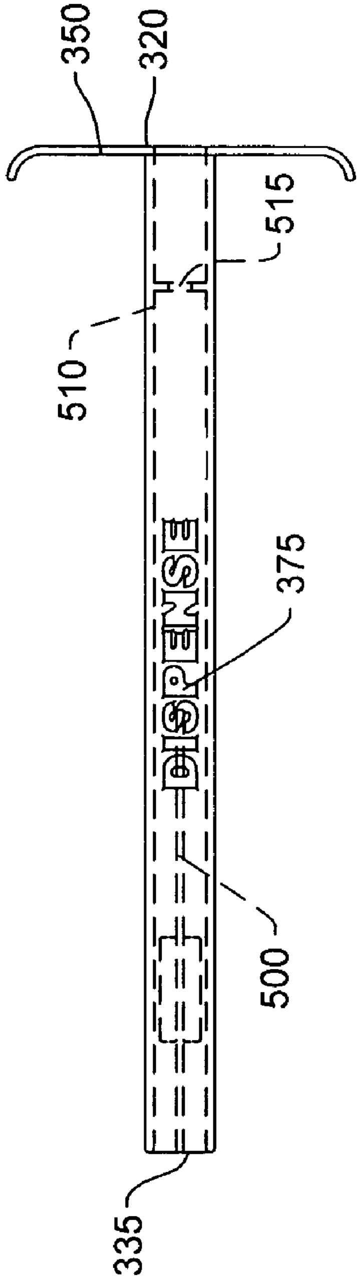
FIG. 10 is a plan view of a reverse side of the housing of FIG. 9.
Figure 11:
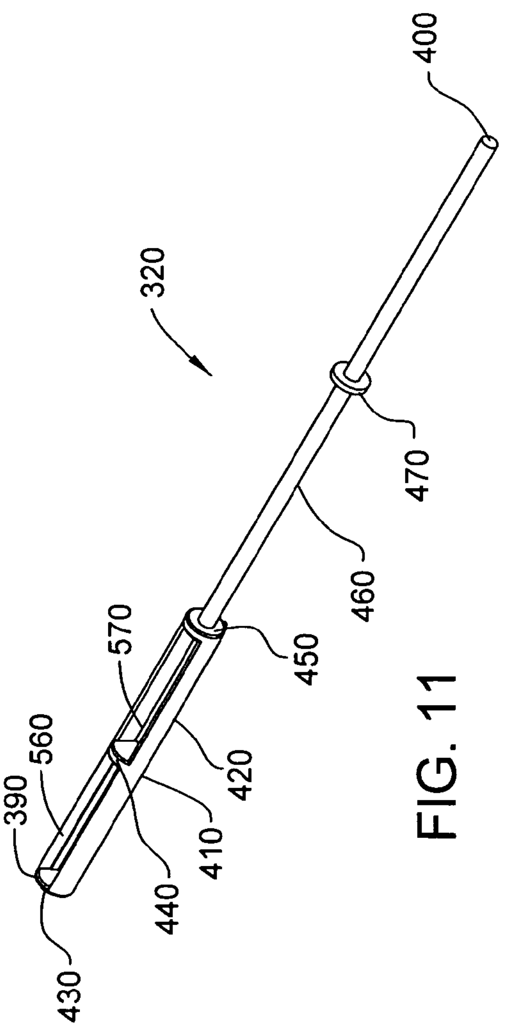
FIG. 11 is a perspective view of a plunger insert for the pill plunger of FIGS. 7-10.
Figure 12:
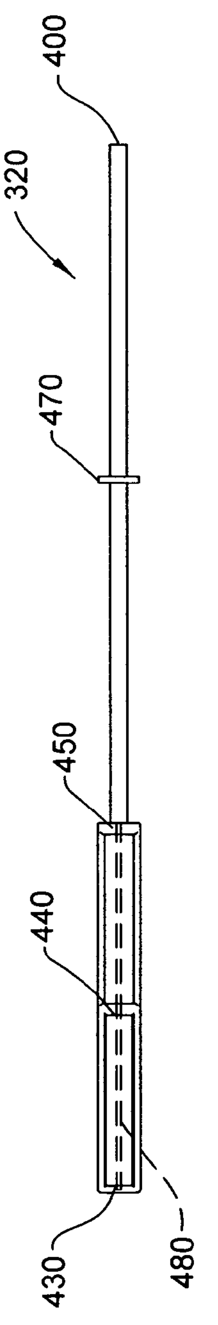
FIG. 12 is a plan view of the plunger insert of FIG. 11.
Figure 13:
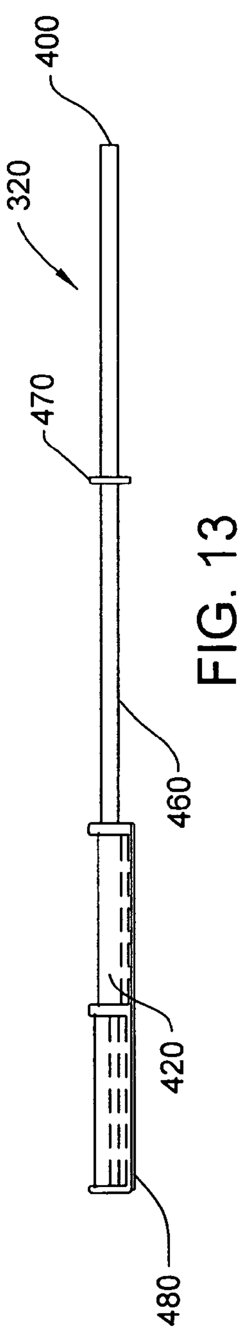
FIG. 13 is a side view of the plunger insert of FIGS. 11-12.
Figure 14:
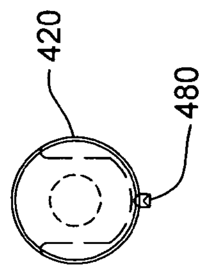
FIG. 14 is an end view of the plunger insert of FIGS. 11-14.

Referring to FIGS. 11-14, an alignment projection 480 is formed on the semi-cylindrical outer wall 420 of the receptacle portion 410. The alignment projection 480 extends outwardly from the wall 420, and is parallel to the longitudinal axis of the plunger insert 320. The alignment projection 480 corresponds to a matching alignment groove 500 (see FIGS. 9-10) formed in the inner wall of the hollow tubular portion 330 of the housing 310. The alignment groove 500 is shown as being centered opposite the window opening 360 and the housing 310.

The interior of the housing 310 further includes a spring stop shoulder 510 having an opening 515 therethrough centered within the interior of the housing 310 for receiving the proximal end 400 of the plunger insert 320. The pill plunger 300 is thus assembled by insertion of the proximal end 400 of the plunger insert 320 into the distal end 335 of the housing 310. The plunger insert 320 is rotated about the longitudinal axis 380 to align the alignment projection 480 with the alignment groove 500. The open top of the receptacle portion 410 is thus aligned with the window 360 of the housing 310. The distal end 400 of the plunger insert 320 passes through the opening 515 in the spring stop shoulder 510 until the stabilizer 470 reaches the spring stop shoulder 510.

As a result, the proximal end 400 of the plunger insert 320 extends beyond the proximal end 340 of the housing 310. The distal end 390 of the plunger insert 320, specifically the distal wall 430 of the receptacle portion 410, is flush with the distal end 335 of the housing 310. To complete the assembly of the pill plunger 300, a thumb button 550 is secured to the proximal end 400 of the plunger insert 320. The thumb button 550 is arranged on the proximal end 400 such that, when fully depressed against the proximal end 340 of the housing 310, the plunger insert 320 will extend beyond the distal end 335 of the housing 310 such that a distal chamber 560 of the receptacle portion 410, defined between the distal wall 430 and the intermediate wall 440, will extend beyond the distal end of the housing 310. The intermediate wall 440 will approximately align with the distal end 335 of the housing 310. A proximal chamber 570, defined between the intermediate wall 440 and the proximal wall 450 of the receptacle portion 410, will then be in alignment with the window 360 of the housing 310, so that the proximal chamber 570 can be charged with a medication. When the plunger insert 320 is in the fully retracted state, the distal chamber 560 will be aligned with the window 360 of the housing 310, and the proximal chamber 570 will be fully contained and sealed within the housing 310 proximally of the window 360.

Figure 15:
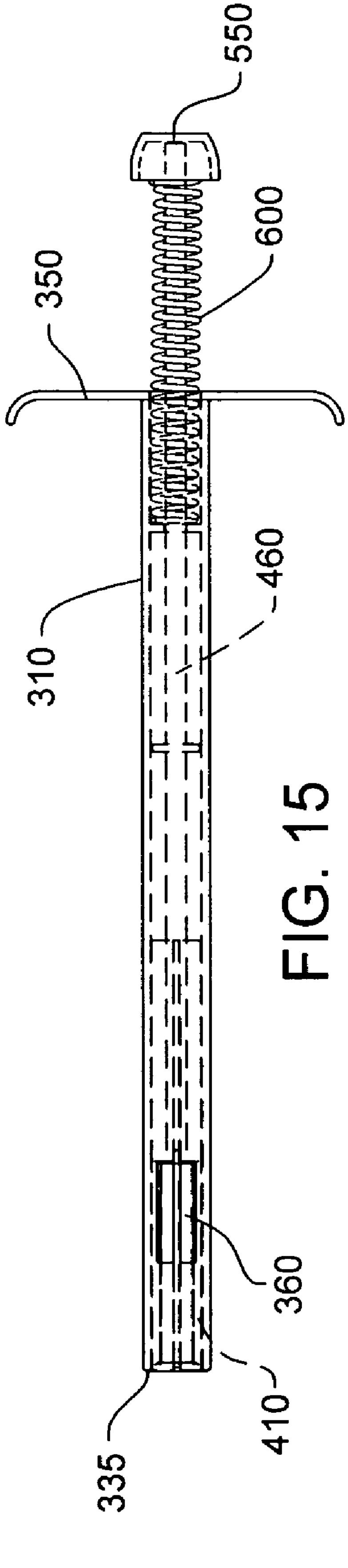
FIG. 15 is a plan view of a further embodiment of a pill plunger according to the invention.

In a further embodiment of the invention, shown in FIG. 15, a coil or compression spring 600 is placed over the proximal end 400 of the plunger insert 320, passing through the opening at the proximal end 340 of the housing 310 and bearing against the spring stop shoulder 510 within the housing 310. The opposing end of the coil or compression spring 600 bears against the base of the thumb button 550 to urge the plunger insert 320 towards its proximal position, with the thumb button 550 extended away from the proximal end 340 of the housing 310, and the distal end 390 of the plunger insert 320 flush with the distal end 335 of the housing 310.

In operation, the embodiments according to FIGS. 7-15 can administer multiple medications, or multi-part medications, by separating the components of the medication between the distal chamber 560 and the proximal chamber 570 of the receptacle portion 410. A further example would be to place a thickened water in the proximal chamber 570 with a medication in the distal chamber 560 to encourage a swallow reflex in the patient and increase the likelihood of proper application of the medication.

In the embodiments of the invention as disclosed above, the pill plunger 100, 300 is placed in a horizontal orientation, with the "LOAD" indicia facing upwardly. The plunger insert 120, 320 is extended distally to expose the receptacle portion 170, 410. The medication is then placed in the receptacle portion and the plunger insert 120, 320 retracted proximally to be enclosed within the housing 110, 310. The pill plunger 100, 300 is then rotated about its longitudinal axis 270, 380, so that the "DISPENSE" indicia is upward. The distal end of the pill plunger 100, 300 is inserted into the patient's mouth. The thumb button 250, 550 is then depressed to extend the plunger insert 120, 320 from the distal end of the pill plunger 100, 300, thereby releasing the medication from the inverted receptacle portion of the plunger insert.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the scope of the appended claims.

What is claimed is:

1. A pill plunger, comprising:

a cylindrical tube having a first end and a second end, and having an inner surface defining an inner diameter;

a flange extending outwardly from the first end of the cylindrical tube;

a plunger insert having a first end and a second end, the first end comprising a thumb button, and the second end comprising a dual receptacle, the dual receptacle having a semi-cylindrical base and first and second end walls, the first and second end walls being substantially circular and having a diameter corresponding to the inner diameter of the cylindrical tube, and an intermediate wall, the first end wall and the intermediate wall defining a first receptacle, and the second end wall and the intermediate wall defining a second receptacle.

2. The pill plunger according to claim 1, further comprising the first and second walls form a seal with the inner surface of the hollow tube.

3. The pill plunger according to claim 1, the cylindrical tube further comprising a window opening in a side wall thereof.

4. The pill plunger according to claim 1, the plunger insert having a first, retracted position within the cylindrical tube, wherein the first receptacle aligns with the window opening.

5. The pill plunger according to claim 1, the plunger insert having a second, extended position within the cylindrical tube, wherein the first receptacle extends beyond the second end of the cylindrical tube.

6. The pill plunger according to claim 1, the plunger insert having a second, extended position within the cylindrical tube, wherein the second receptacle aligns with the window opening.

7. The pill plunger according to claim 1, further comprising a compression spring for biasing the plunger insert into a retracted position.

8. The pill plunger according to claim 1, wherein at least one of the first end wall, the second end wall and the intermediate wall comprises a circumferential groove, and a seal is received in the circumferential groove and engages the inner surface of the cylindrical tube.

9. The pill plunger according to claim 1, the plunger insert further comprising an alignment projection and the cylindrical tube comprising an alignment groove on said inner surface, the alignment projection being received in the alignment groove.

10. A pill plunger, comprising:

a cylindrical tube having a first end and a second end, and having an inner surface defining an inner diameter;

a flange extending outwardly from the first end of the cylindrical tube;

a plunger insert having a first end and a second end, the first end comprising a thumb button, and the second end comprising a receptacle, the receptacle having a semi-cylindrical base and first and second end walls, the first and second end walls being substantially circular and having a diameter corresponding to the inner diameter of the cylindrical tube, wherein the first end wall comprises a first circumferential groove and the second end wall comprises a second circumferential groove and further comprising a seal received in each of the first and second circumferential grooves and engaging the inner surface of the cylindrical tube.

11. The pill plunger according to claim 10, wherein the seal received in each of the first and second circumferential grooves comprises an o-ring.

12. The pill plunger according to claim 8, wherein the seal comprises an o-ring.

* * * * *